(12) United States Patent
Okinishi

(10) Patent No.: US 7,325,926 B2
(45) Date of Patent: Feb. 5, 2008

(54) OPHTHALMOLOGIC PHOTOGRAPHIC DEVICE

(75) Inventor: Satoru Okinishi, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 830 days.

(21) Appl. No.: 10/701,680

(22) Filed: Nov. 4, 2003

(65) Prior Publication Data
US 2004/0090596 A1 May 13, 2004

(30) Foreign Application Priority Data
Nov. 6, 2002 (JP) ............................. 2002-321998

(51) Int. Cl.
A61B 3/14 (2006.01)
(52) U.S. Cl. ...................... 351/210; 351/205
(58) Field of Classification Search ................ 351/205, 351/206, 209–210, 213–216, 221
See application file for complete search history.

(56) References Cited

U.S. PATENT DOCUMENTS 5,237,350 A * 8/1993 Sano ........................... 351/213
5,398,065 A 3/1995 Okino
5,559,552 A 9/1996 Inuiya
2001/0056239 A1 12/2001 Ono ............................ 600/476

FOREIGN PATENT DOCUMENTS

| JP | 10-234669 | * 9/1998 | ................. 351/206 |
| JP | 10 234670 A | 9/1998 | |
| JP | 2000-333906 | 12/2000 | |
| JP | 2000 333906 A | 12/2000 | |
| JP | 2001 137192 A | 5/2001 | |
| JP | 2001 238854 A | 9/2001 | |

* cited by examiner

Primary Examiner—Huy K Mai
(74) Attorney, Agent, or Firm—Morgan & Finnegan, LLP

(57) ABSTRACT

An ophthalmologic photographic device has control means for setting a fixed gain at the time of alignment and at the time of still image taking and switching to AGC when switching to moving image taking, wherein the start gain is determined and set, on the basis of the AGC gain immediate before a shift from moving image taking to alignment or still image taking and the value of the fixed gain during still image taking, by setting means for setting the gain at the time of starting AGC.

5 Claims, 14 Drawing Sheets

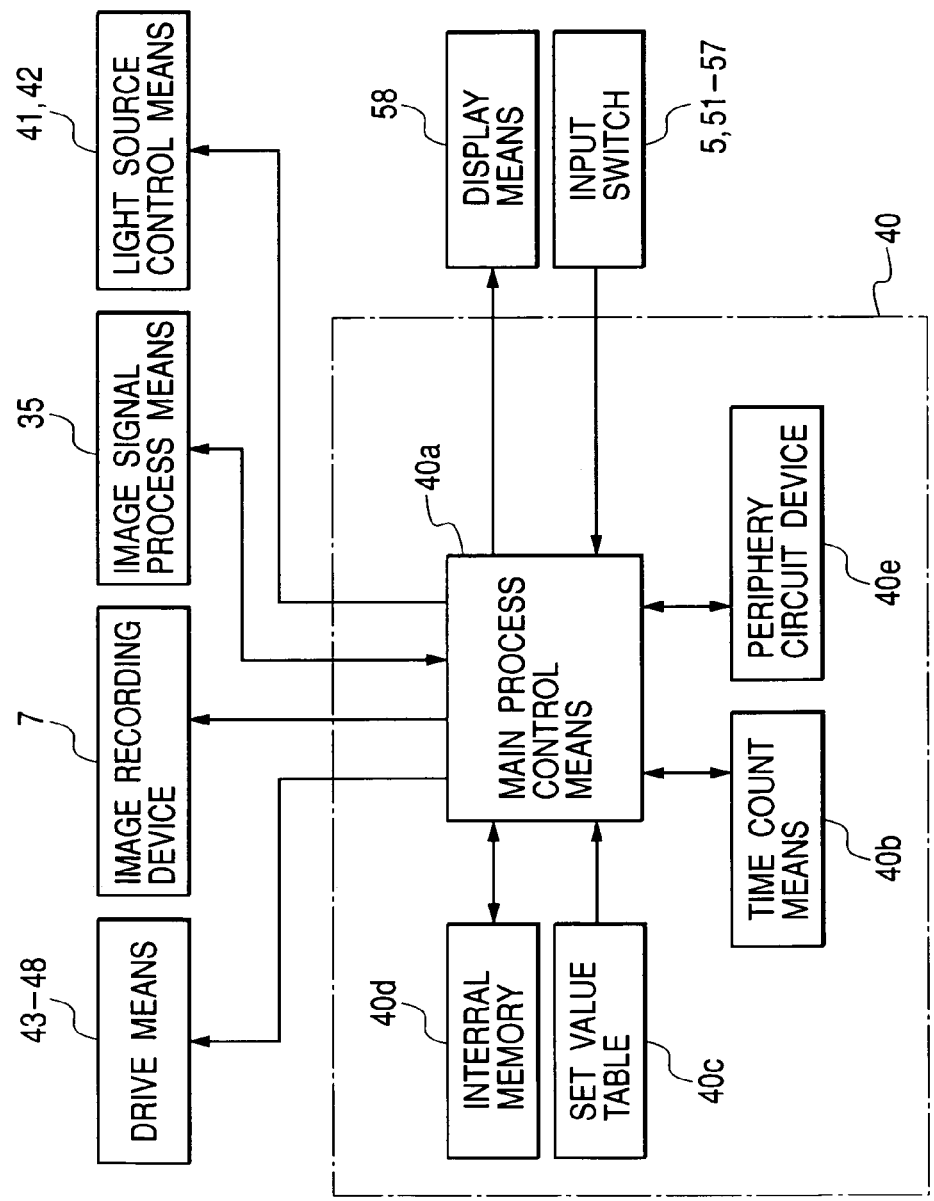

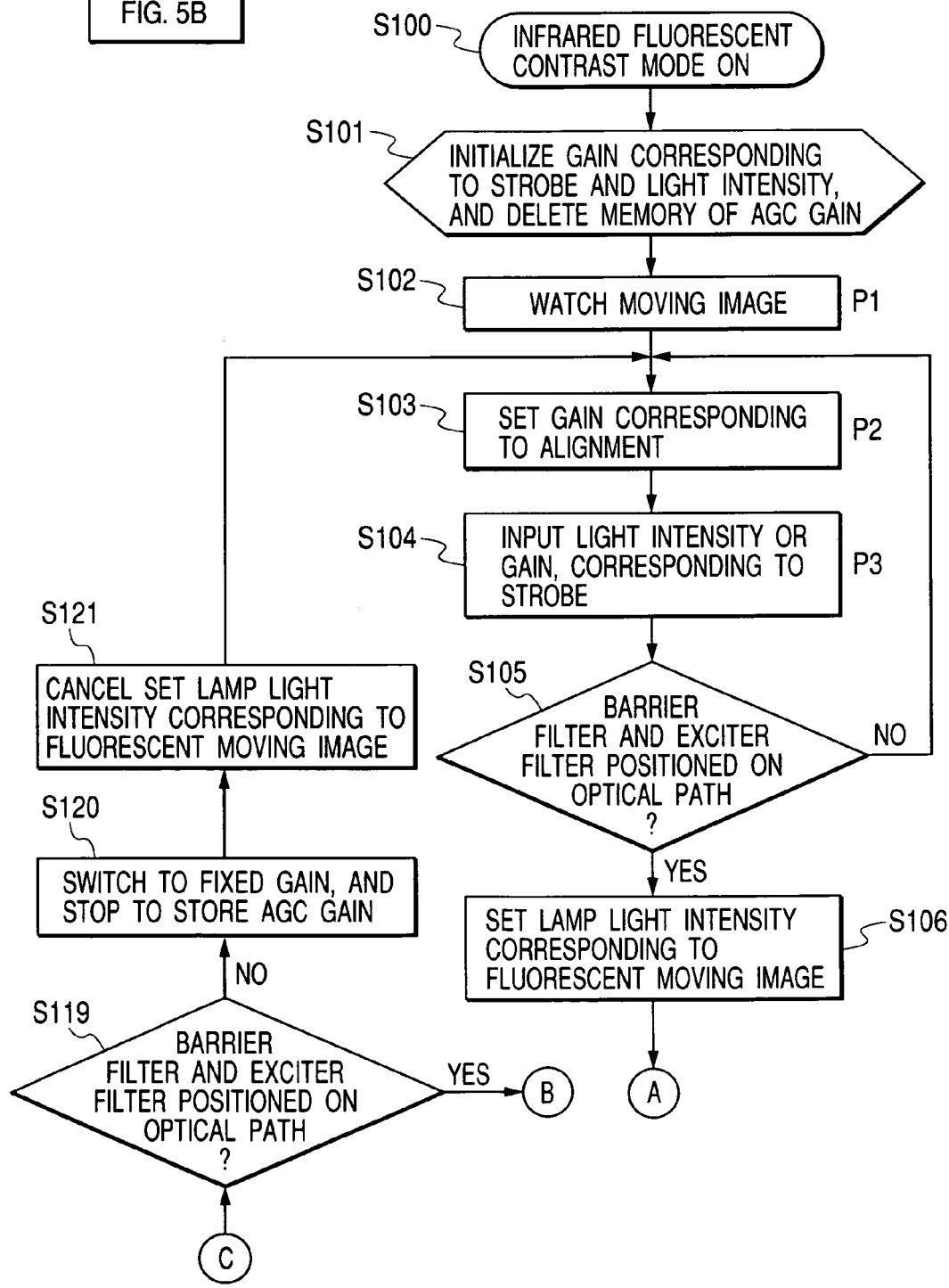

OPHTHALMOLOGIC PHOTOGRAPHIC DEVICE

BACKGROUND OF THE INVENTION

1. Field of the Invention

The present invention relates to an ophthalmologic photographic device for use in ophthalmologic clinics and elsewhere.

2. Related Background Art

The gain of an electronic image pickup element can be regulated mainly by one of the following two methods. By a first method the gain of the image pickup element can be selectively varied as desired, but the gain is fixed, instead of varying with changes in the state of exposure to light, while a second is a so-called auto-gain control (AGC) method, by which the gain automatically varies with changes in the state of exposure to light in which the image pickup element operates.

In electronic photography of ophthalmologic fluorescence contrast imaging in which the brightness of the object varies over time, a gain regulating method like AGC is more suitable where the image is continuously watched or a moving image is to be photographed under continuous illumination with an incandescent lamp or the like.

However, where a very fine image of a higher S/N ratio, i.e. an image free from the superposition of noise, is to be obtained, it is necessary to set the gain of the electronic image pickup element as low as practicable. In such a case, a continuously lit light source which is generally used for ophthalmologic equipment cannot provide sufficient light intensity for illumination, and therefore usually still pictures are taken under strobe lighting using a xenon tube or the like. However, since the exposure time is extremely short in still photography, AGC would lag behind, and no proper gain regulation could be achieved. Therefore, it is necessary to pick up an image with a preset fixed gain.

In an alignment procedure in which the fluorescent image itself need not be picked up, the light coming incident on the image pickup element may be significantly varied by such an external disturbing factor as harmful reflected light from the object eye, and accordingly a stable image is more likely to be obtained by shooting with a fixed gain.

Thus, to obtain a better image, AGC and regulation with a fixed gain are selectively used according to the conditions of use and the shooting conditions.

However, according to the prior art described above, there may be a time lag until regulation by AGC arrives at the right gain where the incident light intensity greatly varies. Moreover, as the gain at the start of AGC is usually fixed to a prescribed level, an image of proper exposure is sometimes impossible to be obtained immediately after a shift to AGC.

SUMMARY OF THE INVENTION

An object of the present invention, therefore, is to obviate the problems noted above, and provide an ophthalmologic photographic device capable of appropriately setting the gain at the time of changing the photographic mode or the like and immediately providing an image of proper exposure.

In order to achieve the object stated above, according to the invention, there is provided an ophthalmologic photographic device so configured as to operate at a fixed amplification rate at the time of alignment and at the time of still image taking and switching to AGC when changing over to moving image taking, wherein the start gain at the time of returning to moving image taking is determined on the basis of the gain immediately before a shift from moving image taking to alignment or still image taking and the value of the fixed gain during still image taking.

This configuration makes it possible to provide an ophthalmologic photographic device capable of properly setting the gain and immediately providing an image of proper exposure at the time of altering the photographic mode or on any other pertinent occasion.

Further objects and configurational aspects of the invention will become more apparent from the subsequent description of the preferred embodiments thereof.

BRIEF DESCRIPTION OF THE DRAWINGS

FIG. 4 shows the configuration of control means;

DETAILED DESCRIPTION OF THE PREFERRED EMBODIMENTS

The present invention will be described in detail with reference to illustrated embodiments thereof.

Figure 1:
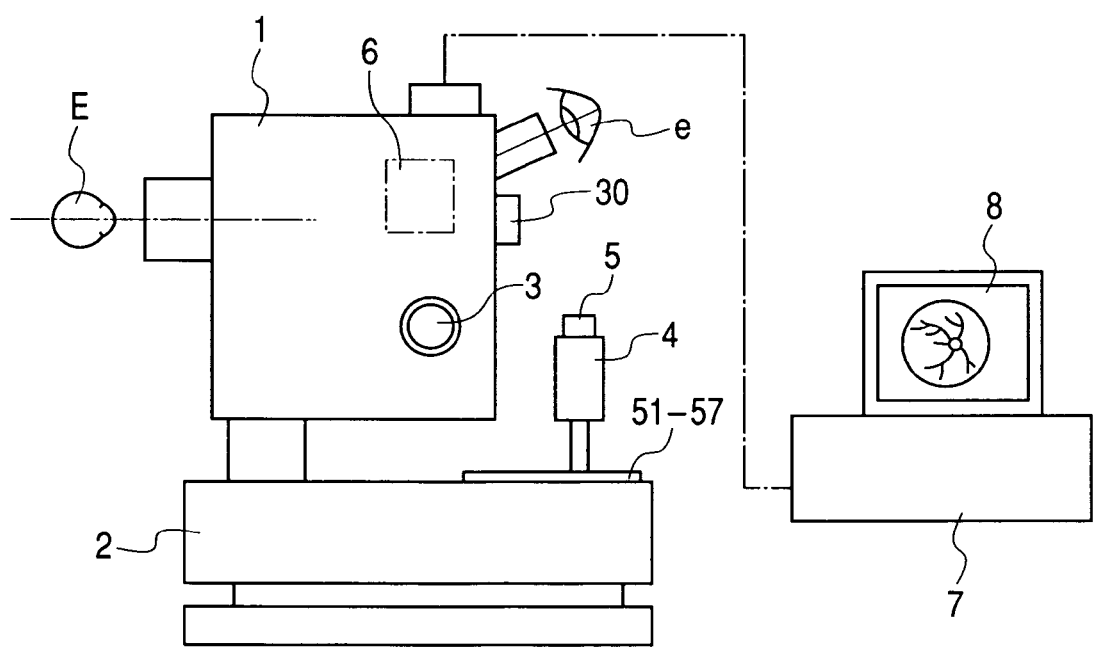
FIG. 1 shows an external view of the device.

FIG. 1 shows an external view of an ophthalmologic photographic device. A photographic device per se 1, installed on a movable base 2, can be freely move up and down, back and forth, and right and left relative to an object eye E within the movable range of the mechanism. The photographic device per se 1 is equipped with a focusing knob 3, and the operation panel on the movable base 2 is provided with a shooting switch 5 and operating switches to be described below, annexed to an operating lever 4. The output of electronic image pickup means 6 built into the photographic device per se 1 is connected by known electrical connecting means to an image recording device 7 and an image displaying device 8 for storing or displaying images, respectively.

Figure 2:
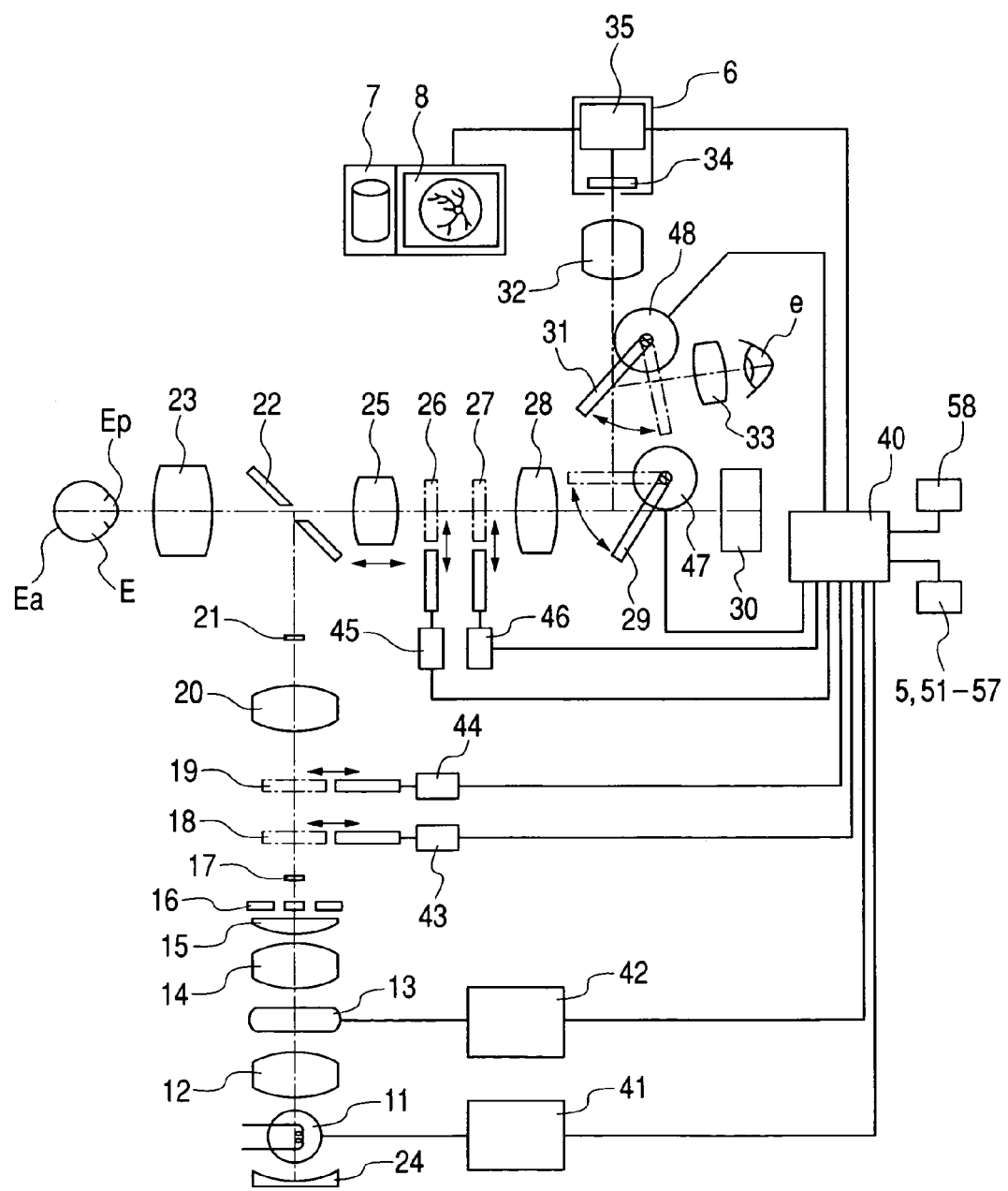
FIG. 2 shows the optical and electrical configuration of the device.

FIG. 2 shows the internal optical and electrical configuration of the photographic device per se 1 and the movable base 2. From a watch light source 11 towards the object eye E, there are arrayed successively a condenser lens 12, a photographic light source 13 consisting of a strobe tube, a condenser lens 14, a field lens 15, a ring slit 16, a shading member 17, a visible fluorescence exciter filter 18 that can be freely positioned on or off an optical path, a similar infrared fluorescence exciter filter 19, a relay lens 20, a shading member 21, a bored mirror 22 and an objective lens 23 to constitute an illuminating optical system. Further, behind the watch light source 11 is arranged a concave mirror 24.

In the watch and photographic optical system behind the bored mirror 22, there are successively arrayed a focusing lens 25, a visible fluorescence barrier filter 26 that can be freely positioned on or off an optical path, a similar infrared fluorescence barrier filter 27, an imaging lens 28, a first spring-up mirror 29, and image pickup means 30 consisting of a silver salt film camera, for instance.

In the reflecting direction of the first spring-up mirror 29, there are provided a second spring-up mirror 31, an electronic imaging lens 32 and the electronic image pickup means 6. In the reflecting direction of the second spring-up mirror 31 is provided an eyepiece 33, which enables the examiner's eye e to watch the object eye E.

The electronic image pickup means 6 consists of an electronic image pickup element 34 and image signal process means 35, and the output of the electronic image pickup means 6 is connected to the image displaying device 8 and the image recording device 7.

To control means 40 taking charge of all the controls over the device are connected light source control means 41 and 42 for respectively controlling the watch light source 11 and the photographic light source 13, drive means 43, 44, 45 and 46 for respectively operating the exciter filters 18 and 19 and the barrier filters 26 and 27, drive means 47 and 48, each consisting of a solenoid, for respectively driving the spring-up mirrors 29 and 31, and the electronic image pickup means 6. The drive means 43, 44, 45, 46, 47 and 48 may as well consist of known actuators whose operations can be electrically controlled, such as motor pneumatic cylinders or hydraulic cylinders, instead of solenoids.

Figure 3:
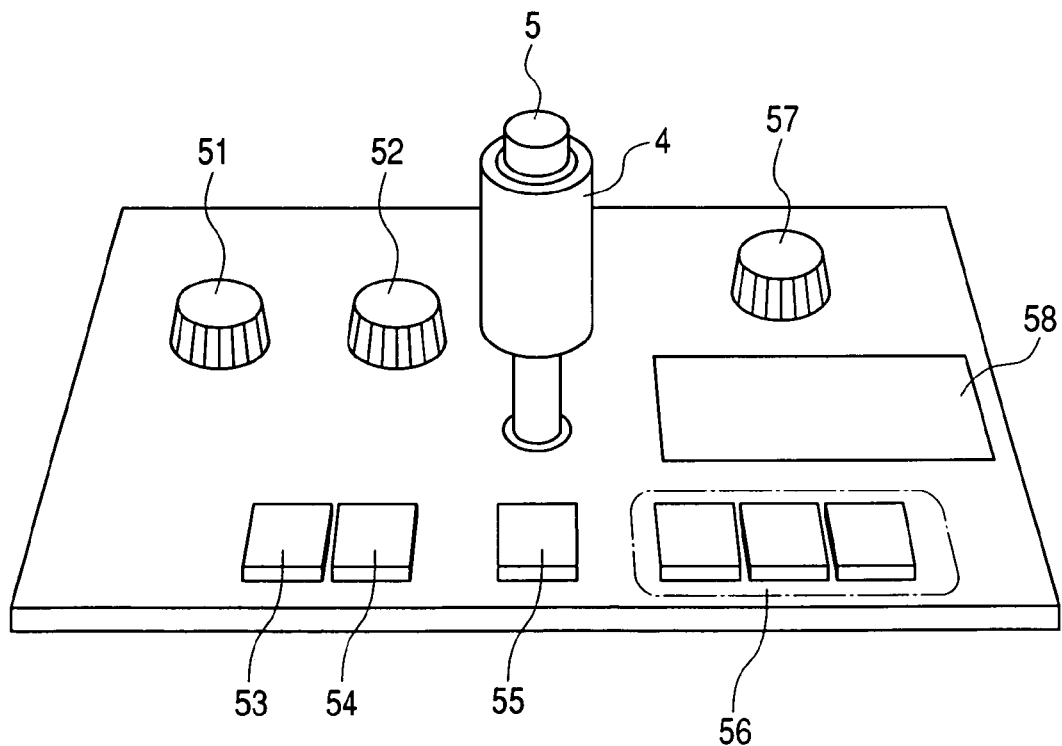
FIG. 3 shows a perspective view of an operation panel.

Further connected to the control means 40 are a lamp dimmer dial 51 for setting the light intensity of the watch light source 11 on the operation panel shown in FIG. 3, a strobe dimmer dial 52 for setting the light intensity of the photographic light source 13, an exciter switch 53 for operating the positioning of the visible fluorescence exciter filter 18 for visible fluorescence contrast photography and the infrared fluorescence exciter filter 19 for infrared fluorescence contrast photography on and off the optical path, a barrier switch 54 for operating the positioning of the visible fluorescence barrier filter 26 for visible fluorescence contrast photography and the infrared fluorescence barrier filter 27 for infrared fluorescence contrast photography on and off the optical path, a timer switch 55 for starting/stopping a timer, a mode switch 56 for switching the photographic mode, a gain dial 57 for setting the fixed gain of the image signal process means 35, and display means 58 for displaying the signal amplification rates of the timer and the electronic image pickup means 6, the light intensity of illumination, the photographic mode and so forth.

As shown in FIG. 4, the control means 40 consists of main process control means 40a for controlling the operations of various parts of the device, controlling various operating modes, arithmetic processing, circumferential judgment and so forth, time count means 40b for generating time count information, a set value table 40c for storing light intensity, gain and various set values regarding the control of the device, an internal memory 40d for temporarily storing input values from outside, various set values read out of the set value table for control purposes, and the points of time when data were entered or processed, and a periphery circuit device 40e for assisting the main process control means 40a.

The control means 40, receiving inputs from the shooting switch 5 and operating switches 5 and 51 through 57, alters the contents of controls, and displays on the display means 58 the light intensity, gain, photographic mode and so forth.

Illuminating light emitted from the continuously emitting watch light source 11 whose light emission is controlled by the light source control means 41 and from the photographic light source 13 whose light emission is controlled by the light source control means 42 passes the condenser lens 12, and formed into a ring shape by the field lens 15 and the ring slit 16. The illuminating light formed into a ring shape passes the relay lens 20 and the shading members 17 and 21 against harmful light, is deflected by the bored mirror 22 and irradiates the object eye E via the objective lens 23.

The reflected light from the object eye E again passes the objective lens 23, the hole of the bored mirror 22, the focusing lens 25 and the imaging lens 28 both movable in the direction of the optical axis, and reaches the first spring-up mirror 29. If the first spring-up mirror 29 is off the optical path, the reflected light from the object eye E will reach the image pickup means 30, and the image of a prescribed region of the object eye E will be taken. If the first spring-up mirror 29 is on the optical path, the reflected light will reach the second spring-up mirror 31.

If the second spring-up mirror 31 is on the optical path, the reflected light from the object eye E will pass the eyepiece 33 and forms an image on the examiner's eye e to enable him or her to watch the object eye E by direct vision. If the second spring-up mirror 31 is off the optical path, the reflected light will pass the electronic imaging lens 32 and reach the electronic image pickup means 6.

The image signal output of the reflected light formed into an image on the electronic image pickup element 34, after undergoing signal amplification by the image signal process means 35 with a prescribed gain, is delivered to the image recording device 7 and the image displaying device 8 for storage and displaying, respectively. The image signal process means 35 can amplify image signals in one of two amplification modes including one with a fixed gain entailing no variation in set value and the other by AGC under which a proper gain calculated from the image signals entered from the electronic image pickup element 34 is set, and switching between these two amplification modes can be achieved by control with the control means 40.

The image signal process means 35 externally outputs in a moving image the image signals picked up by the electronic image pickup element 34 or stores an image in synchronism with light emission by the photographic light source 13 to output it externally. The switching between these moving image output and still image output, the distribution of a synchronizing signal of the time of still image taking and the operation control of the image recording device 7 are accomplished by the control means 40. Further, the control means 40 stores a plurality of gains to be set in the fixed gain mode and a plurality of gains to be automatically set under AGC into the internal memory 40d, and sets the start gain that is set when AGC starts.

The exciter filters 18 and 19 extract from the illuminating light only exciting light for causing a prescribed fluorescence contrast medium to generate fluorescence. The barrier filters 26 and 27 block only exciting light out of fluorescent light and reflected exciting light from the object eye E. This function applies in the same way to both visible light and infrared light.

Incidentally, the exciter switch 53 and the barrier switch 54 work on the visible fluorescence exciter filter 18 and the visible fluorescent the barrier filter 26 if the photographic mode is the visible fluorescence contrast mode, or on the infrared fluorescence exciter filter 19 and the infrared fluorescence barrier filter 27 if the photographic mode is the infrared fluorescence contrast mode. The switching between these functions is accomplished by the control means 40.

Figure 5B:
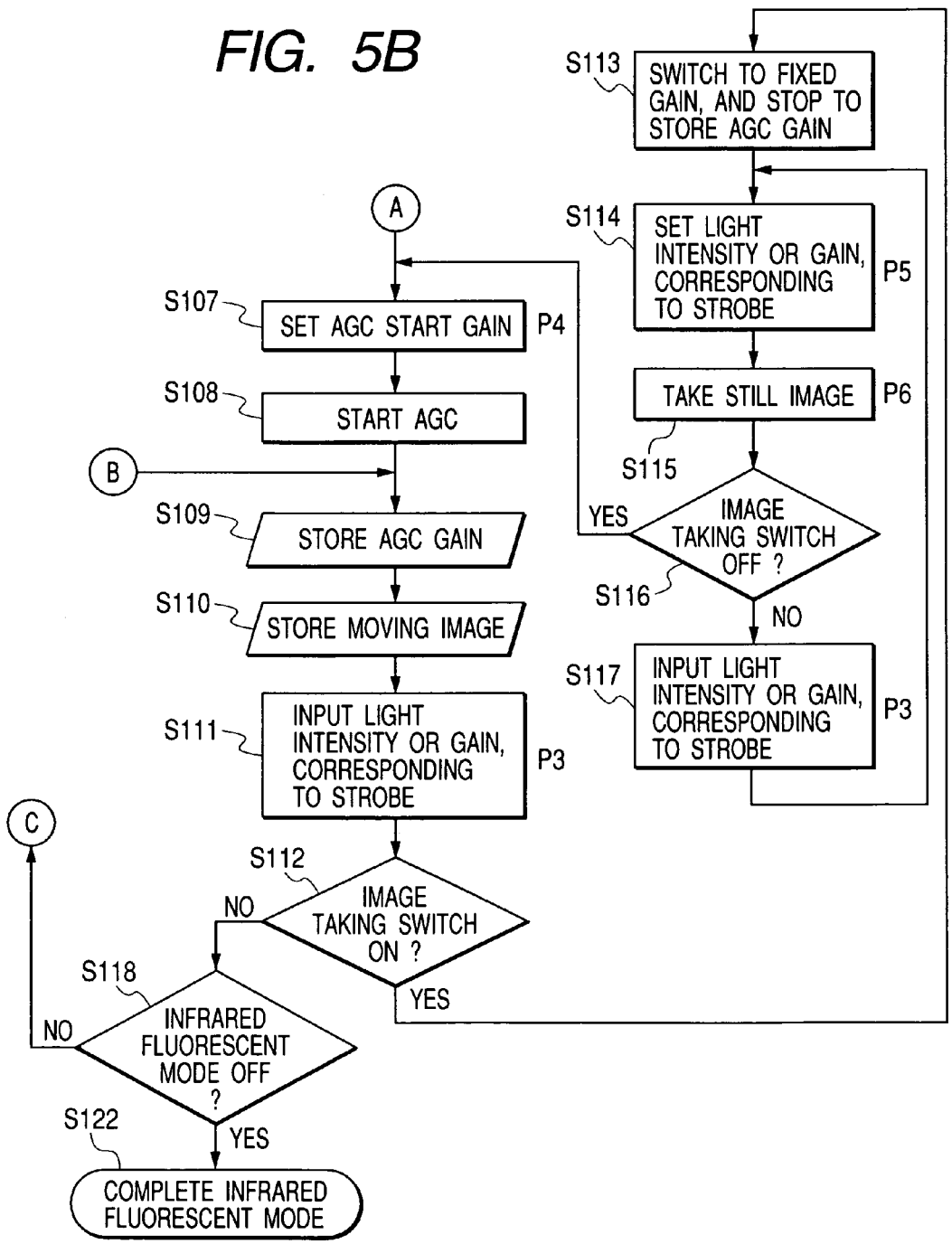
FIG. 5 is comprised of FIGS. 5A and 5B showing flow charts of device control by the control means in an infrared fluorescence contrast mode.

FIGS. 5A and 5B are flow charts of device control by the control means 40 in the infrared fluorescence contrast mode. The flow consists of a program of many steps, consisting of step S100 through step S122. As required, some of the individual steps will be described in detail as sub-programs with reference to FIG. 6 through FIG. 11, and the parenthesized step number of the sub-program will follow each corresponding description below. To add, P1 through P6 stated at steps S102, S103, S104, S107, S111, S114, S115 and S117 denote the flow charts of sub-programs respectively shown in FIG. 6 through FIG. 11.

At step S100, the control means 40 will cause the first spring-up mirror 29 to stay on the optical path and the second spring-up mirror 31 to go off the optical path if the infrared fluorescence contrast mode is selected with the mode switch 56.

At step S101, the control means 40 deletes the memorized AGC gain from the internal memory 40d as an initialization procedure, and stores prescribed initial values recorded in the internal set value table 40c into the internal memory 40d as the gain corresponding to the strobe and the light intensity of strobe emission.

Figure 6:
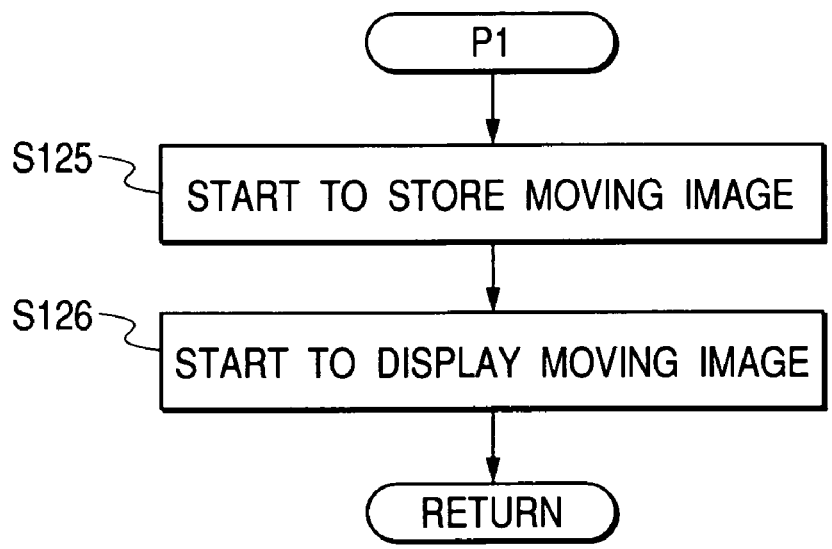
FIG. 6 is a flow chart of a sub-program of the flow of FIGS. 5A and 5B.

At step S102, as shown in the flow chart of sub-program P1 in FIG. 6, the control means 40 causes the electronic image pickup means 6 to start storing the image of the examined eye in a moving image (step S125), the image to be displayed on the image displaying device 8 (step S126), and the alignment mode to start.

Figure 7:
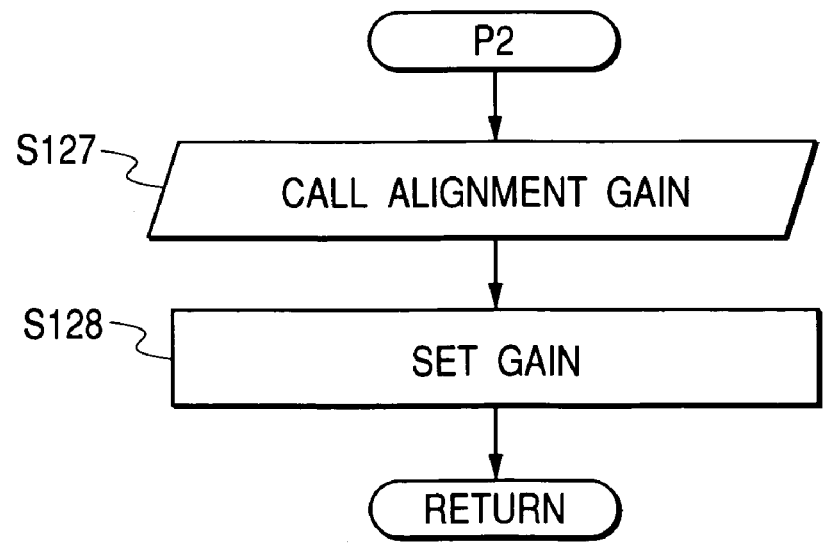
FIG. 7 is a flow chart of another sub-program of the flow of FIGS. 5A and 5B.

At step S103, as shown in the flow chart of sub-program P2 in FIG. 7, the control means 40 calls the gain corresponding to alignment recorded in the set value table 40c (step S127), and sets it as the fixed gain of the image signal process means 35 (step S128).

Figure 8:
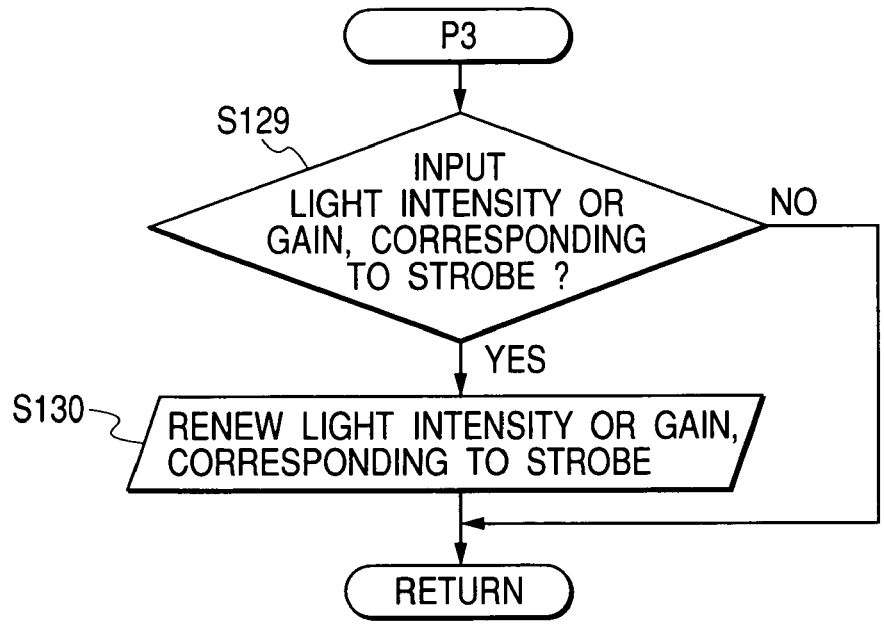
FIG. 8 is a flow chart of another sub-program of the flow of FIGS. 5A and 5B.

At step S104, as shown in the flow chart of sub-program P3 in FIG. 8, the control means 40, if any value of light intensity or gain is entered with the strobe dimmer dial 52 or the gain dial 57, respectively (step S129), replaces the pertinent memorized value in the internal memory 40d with that value as the strobe light intensity or the gain corresponding to the strobe (step S130). If there is no input, the pertinent memorized value of the strobe light intensity or the gain corresponding to the strobe in the internal memory 40d will remain what it was at the time of initialization (step S129).

The examiner performs alignment relative to the object eye E while watching the moving image on the image displaying device 8, administers a fluorescence contrast medium to the examined person, and at the same time presses the timer switch 55 to start the timer; when the exciter switch 53 and the barrier switch 54 are pressed at step S105, the infrared fluorescence exciter filter 19 and the infrared fluorescence barrier filter 27 are positioned onto the optical path, and the mode shifts to the fluorescent moving image mode.

At step S106, to match the light intensity of the lamp to a fluorescent moving image, the control means 40 raises the light intensity of the watch light source 11 by a prescribed value stored in the set value table 40c. Incidentally, the light intensity of the lamp is monitored by the control means 40 all the time and, at the time of a mode shift between the alignment mode and the fluorescent moving image mode, the light intensity that is determined by the monitoring is varied by the aforementioned prescribed value stored in the set value table 40c.

Figure 9:
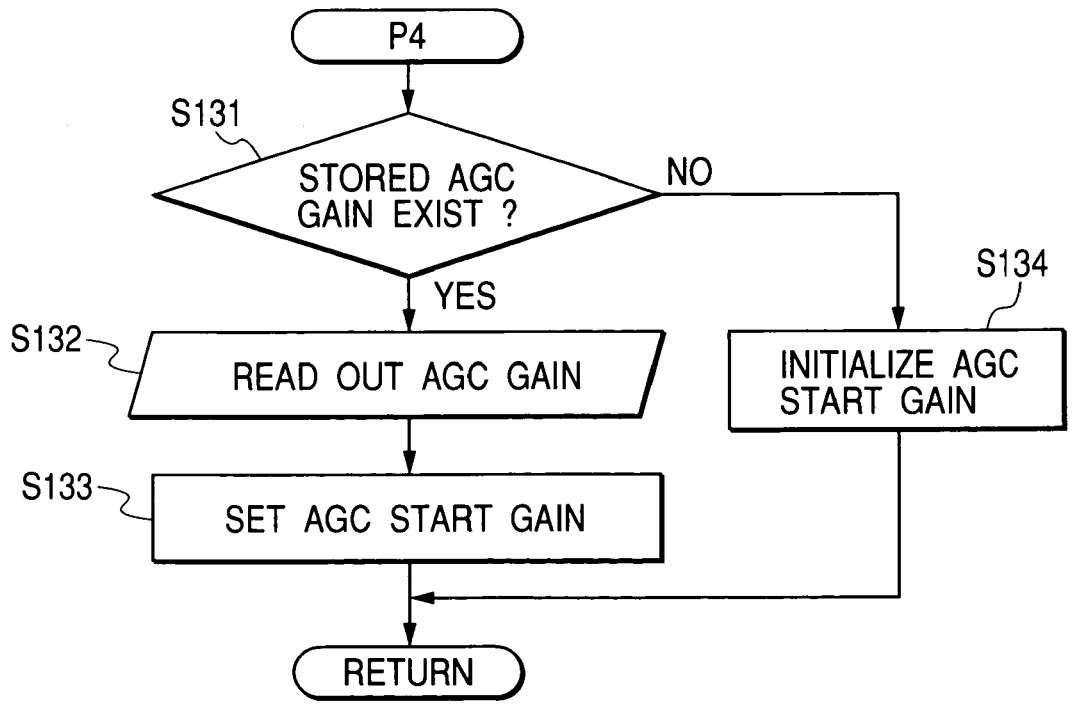
FIG. 9 is a flow chart of another sub-program of the flow of FIGS. 5A and 5B.

At step S107, since there is no memorized AGC gain in the internal memory 40d of the control means 40 (step S131), the control means 40 sets the prescribed value stored in the set value table 40c as the AGC start gain of the image signal process means 35 as shown in the flow chart of sub-program P4 in FIG. 9 to initialize the AGC start gain (step S134).

At step S108, the control means 40 switches the image signal process means 35 to the AGC mode. At step S109, the AGC gain supplied from the image signal process means 35 is consecutively stored into the internal memory 40d at prescribed intervals of time, and at step S110 the image recording device 7 is instructed to start recording the fluorescent moving image.

At step S111, as at step S104, the strobe light intensity or the gain corresponding to strobe-lit shooting can be entered. As shown in the flow chart of FIG. 8, the control means 40, if any value of light intensity or gain is entered with the strobe dimmer dial 52 or the gain dial 57, respectively (step S129), replaces the pertinent memorized value in the internal memory 40d with that value as the strobe light intensity or the gain corresponding to the strobe (step S130). If there is no input, the previously entered value of the strobe light intensity or the gain corresponding to the strobe in the internal memory 40d will not be renewed (step S129).

If the shooting switch 5 is pressed at step S112, the mood will shift to the fluorescent still image mode. At step S113, the control means 40 switches the image signal process means 35 to a fixed gain, and stops storing the AGC gain into the internal memory 40d.

Figure 10:
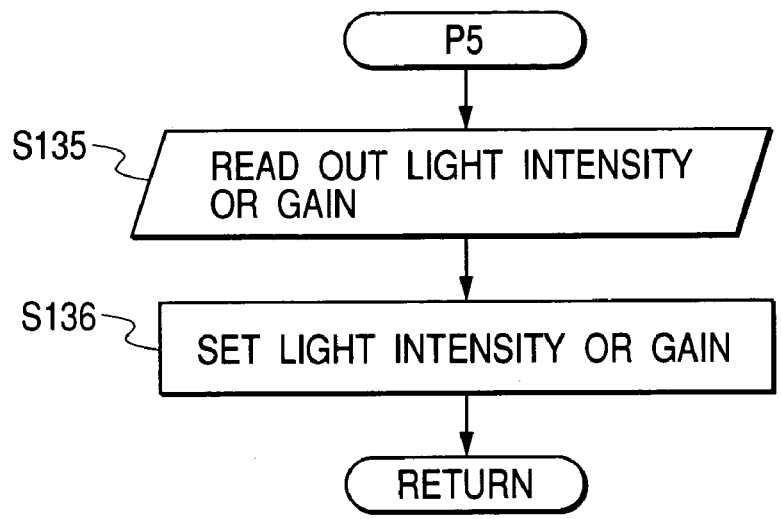
FIG. 10 is a flow chart of another sub-program of the flow of FIGS. 5A and 5B.

At step S114, as shown in the flow chart of sub-program P5 in FIG. 10, the control means 40 reads out of the internal memory 40d the strobe light intensity and the gain corresponding to the strobe entered at step S104 or step S111 and stored into the internal memory 40d of the control means 40 (step S135), and sets the light source control means 42 and the image signal process means 35 to respective fixed gains (step S136).

Figure 11:
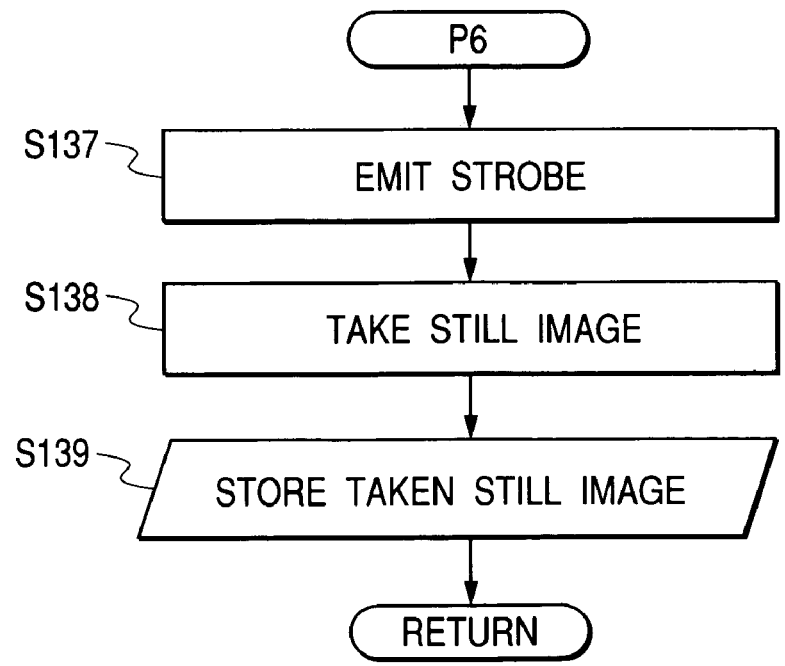
FIG. 11 is a flow chart of another sub-program of the flow of FIGS. 5A and 5B.

At step S115, as shown in the flow chart of sub-program P6 in FIG. 11, the control means 40 causes the photographic light source 13 to emit light with the light intensity set at step S114 (step S137), causes the electronic image pickup means 6 to take a still image of the object eye E in synchronism with the light emission (step S138), and records with the gain set at step S114 the image signals, amplified by the image signal process means 35, into the image recording device 7 (step S139). The photographed image can as well be displayed as it is taken.

If the shooting switch 5 is kept pressed at step S116, consecutive shooting will take place to return to step S114, and if the shooting switch 5 is released, a return to step S107 in the fluorescent moving image mode will take place. During the return to step S114, it will become possible to enter light intensity and gain at step S117 as at step S104 or step S111.

If a shift from the fluorescent still image mode to the fluorescent moving image mode takes place at step S107, since an AGC gain is stored in the internal memory 40*d* of the control means 40 as shown in the flow chart of FIG. 9 (step S131), the AGC start gain setting is accomplished by reading, within a prescribed period of time before shifting from the fluorescent moving image mode to the fluorescent still image mode at step S112, the latest AGC gain stored in the internal memory 40*d* (step S132) and setting it in the image signal process means 35 as the AGC start gain (step S133).

Thereafter, until the shooting switch 5 is pressed at step S112, fluorescent moving image recording whose gain is controlled by AGC will continue. If at least either of the exciter switch 53 and the barrier switch 54 is operated during fluorescent still image recording at step S119 and at least either of the infrared fluorescence exciter filter 19 and the infrared fluorescence barrier filter 27 goes off the optical path, the fluorescent moving image mode will stop. At step S120, the control means 40 switches the image signal process means 35 to a fixed gain, and stops storing the AGC gain into the internal memory 40*d*.

At step S121, the light intensity of the lamp is returned to its level before the shift to fluorescent moving image mode, and a shift to the alignment mode takes place. Setting of the AGC start gain again at step S107 in connection with a shift to the fluorescent moving image mode, as an AGC gain is stored in the internal memory 40*d* of the control means 40, is accomplished by reading within a prescribed period time before shifting to the alignment mode (step S132) the latest AGC gain stored in the internal memory 40*d* as shown in the flow chart of FIG. 9, and setting it in the image signal process means 35 as the AGC start gain (step S133).

Although the foregoing description concerned device control operations in the infrared fluorescence contrast mode by way of an example, exactly the same controls can be applied to a visible fluorescence environment if set values, members and operating switches for exclusive infrared use are replaced with ones exclusively intended for visible light use.

In this embodiment of the invention, the initialization of the AGC start gain at step S107 is supposed to begin in the alignment mode and to be accomplished only when a shift to the fluorescent moving image mode has taken place. However, if the conditions of judgment at step S131 in FIG. 9, which shows the details of step S107, are altered, the conditions of initialization can be set in many different ways. For instance, setting can be so made that a shift to the fluorescent moving image mode can be accomplished only when the timer switch 55 is pressed.

Further by setting the initial value in the setting table for initializing the AGC start gain to the maximum gain, it is made possible to catch a fluorescent image in an early phase of fluorescent moving image shooting.

Figure 12:
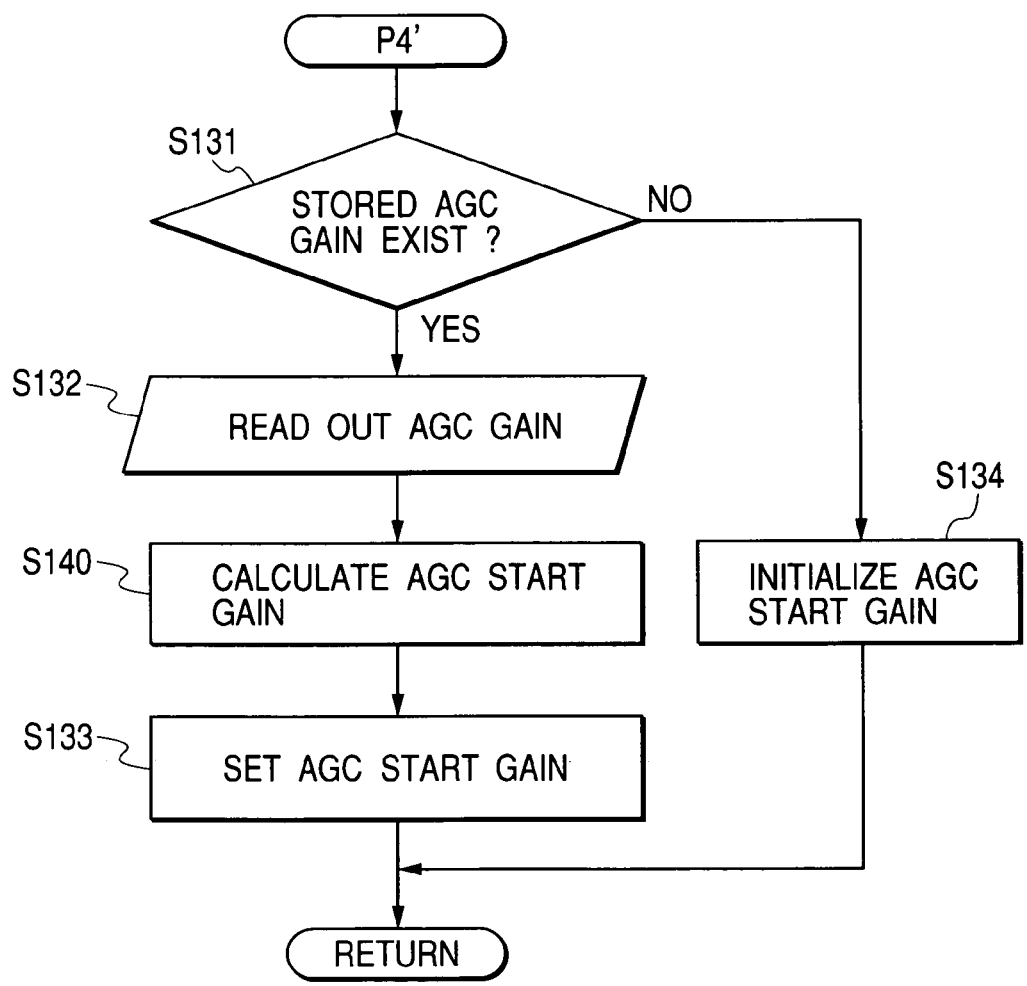
FIG. 12 is a flow chart of another sub-program of the flow of FIGS. 5A and 5B.

FIG. 12 is the flow chart of sub-program P4', in which step S140 of start gain calculation is added between step S132 and step S133 of the flow chart shown in FIG. 9, and shows a second method of setting the AGC start gain at step S107.

Figure 13:
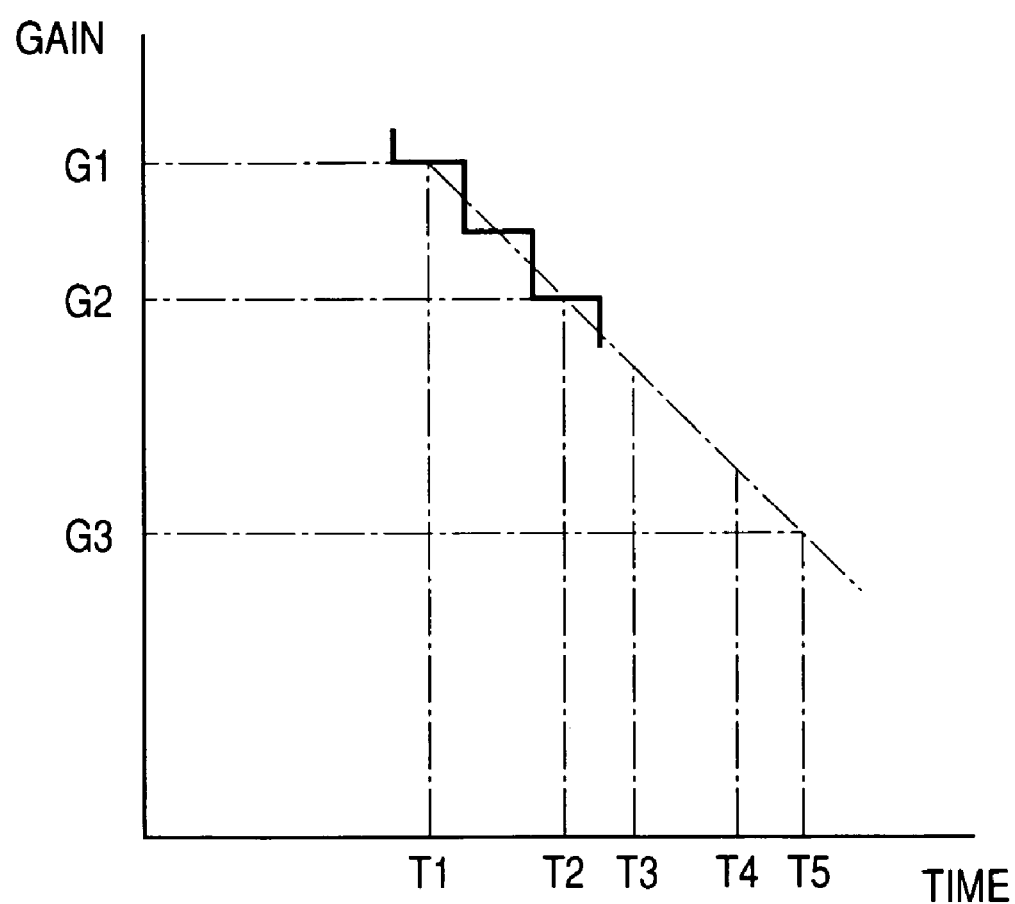
FIG. 13 illustrates the principle of a method of calculating and setting the AGC start gain from a plurality of gain records.

To explain the calculation which is done at step S140 with reference to FIG. 13, the solid lines show a cutout of the variations of the gain over time under AGC before the shift from the fluorescent moving image mode to the fluorescent still image mode, wherein the horizontal axis represents the time, and the vertical axis, the gain. The time at which the shooting switch 5 is pressed and the fluorescent still image mode starts is T3, that at which the fluorescent still image mode has ended is T4, and that at which the fluorescent moving image mode is restarted is T5. At the times T1 and T2 before the shift to the fluorescent still image mode, the respective gains G1 and G2 are stored into the internal memory 40*d* together with the times. Supposing that the varying rate of the gain between the time T1 and the time T2 remains unchanged until the time T5, the gain G5 at the time T5 is represented by the following equation (1).

$$G5 = G1 - \{(T5-T1) \times (G1-G2)\}/(T2-T1) \qquad (1)$$

By storing two or more AGC gains and recording times in the internal memory 40*d* all the time at step S109 in the flow chart of FIGS. 5A and 5B and calculating the aforementioned gains G1 and G2 and times T1 and T2 by Equation (1) at step S132 of the flow chart shown in FIG. 11, the AGC start gain G5 at the time of resuming the fluorescent moving image mode can be accurately figured out. The gain G5 thereby obtained is set in the image signal process means 35 at step S133 as the AGC start gain.

Figure 14:
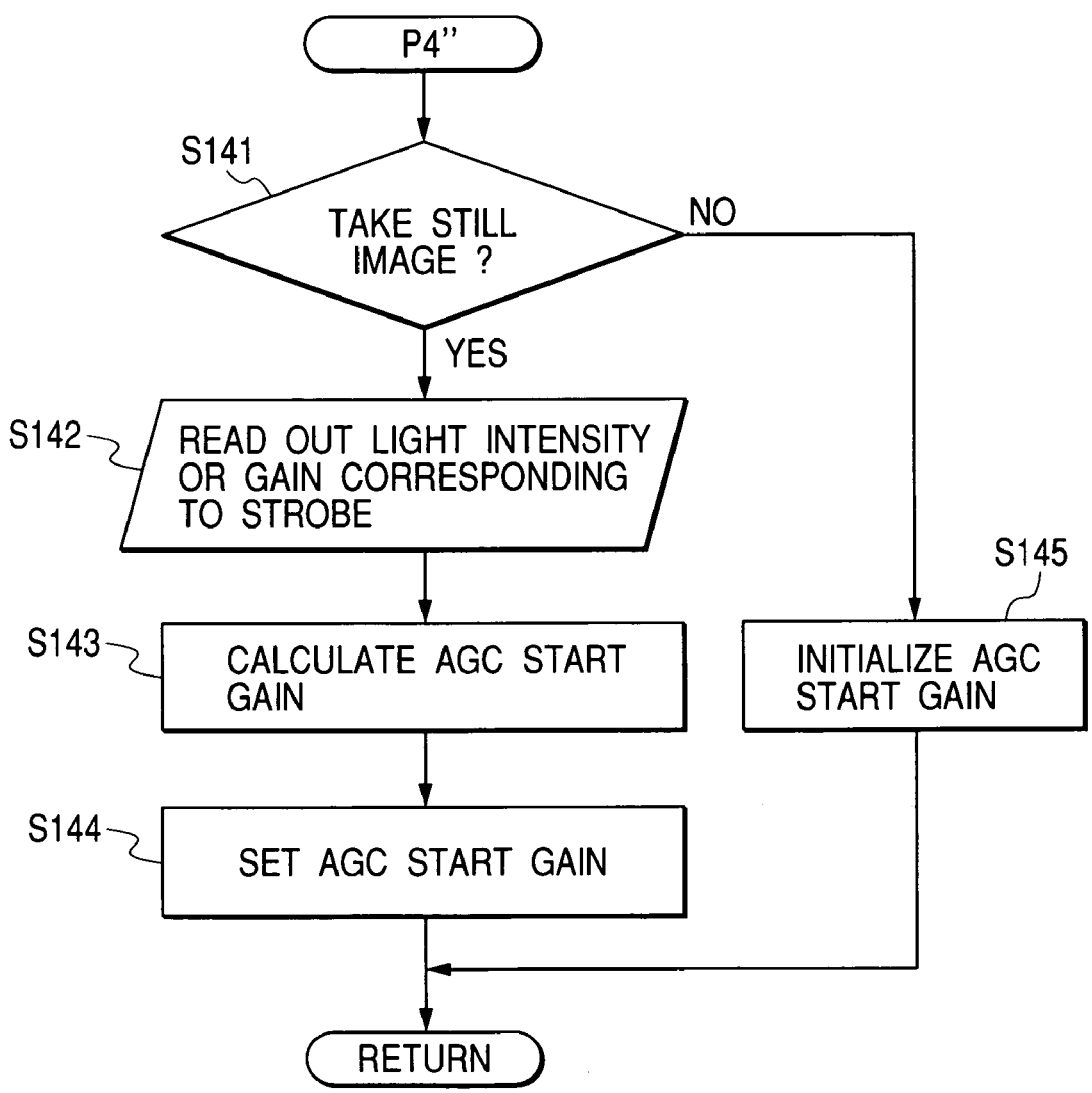
FIG. 14 is a flow chart of another sub-program of the flow of FIGS. 5A and 5B.

FIG. 14 is the flow chart of sub-program P4" under which no AGC gain is used for determining the AGC start gain, but the strobe light intensity and the gain corresponding to the strobe are used. Applying FIG. 14 to step S107 in FIGS. 5A and 5B makes step S109 in FIGS. 5A and 5B not absolutely necessary.

When a shift takes place from the fluorescent still image mode to the fluorescent moving image mode, as still image taking has already taken place by the time step S141 in FIG. 14 is reached, a shift to step S142 takes place, and the strobe light intensity and the gain corresponding to the strobe stored in the internal memory 40*d* is read out. At step S143, calculation by the following Equation (2) is performed, where Gm is the AGC start gain, Gf, the gain corresponding to the strobe, Pf, the strobe light intensity and Pm, the light intensity of the lamp.

$$Gm = Gf \times Pf/Pm \qquad (2)$$

The value of Gm thereby figured out is set in the image signal process means 35 at step S144 as the AGC start gain.

Figure 15:
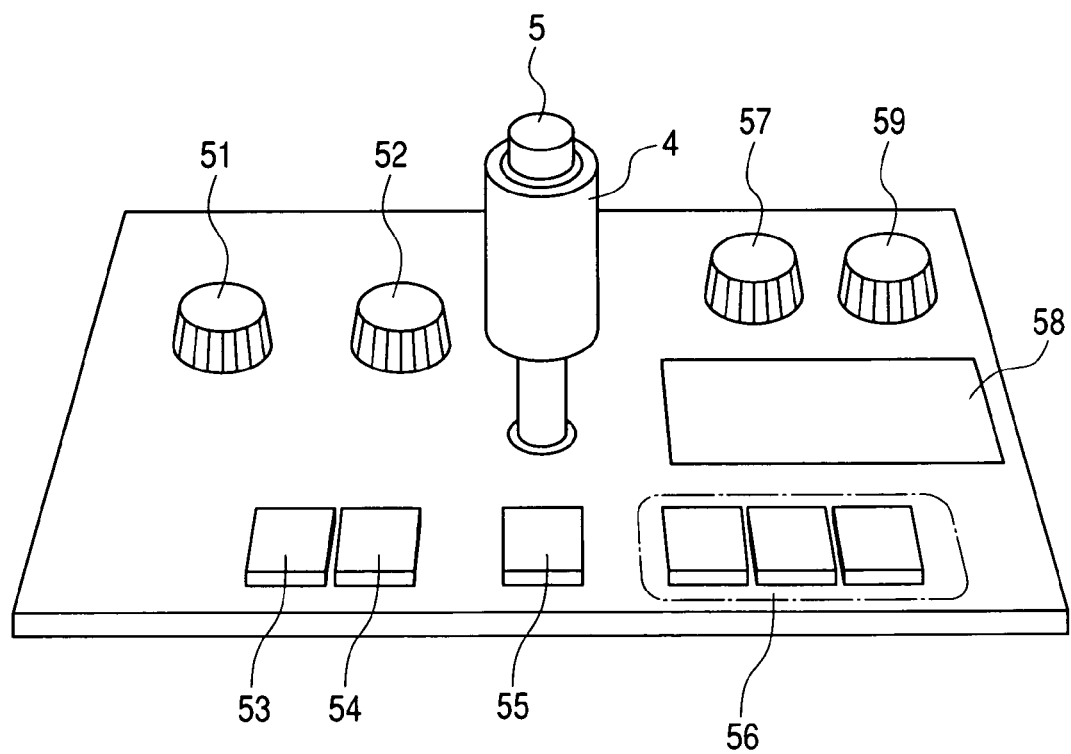
FIG. 15 shows a perspective view of another version of the operation panel.

As shown in FIG. 15, a start gain dial 59 for setting the AGC start gain may be provided on the operation panel so that the AGC start gain can be altered by manually entering it into the control means 40. In this case, if the AGC start gain is initialized in advance as a prescribed value in the set value table 40*c* at step S101 in FIG. 4, standard fluorescent moving image taking will be made possible without having to enter the start gain.

Figure 16:
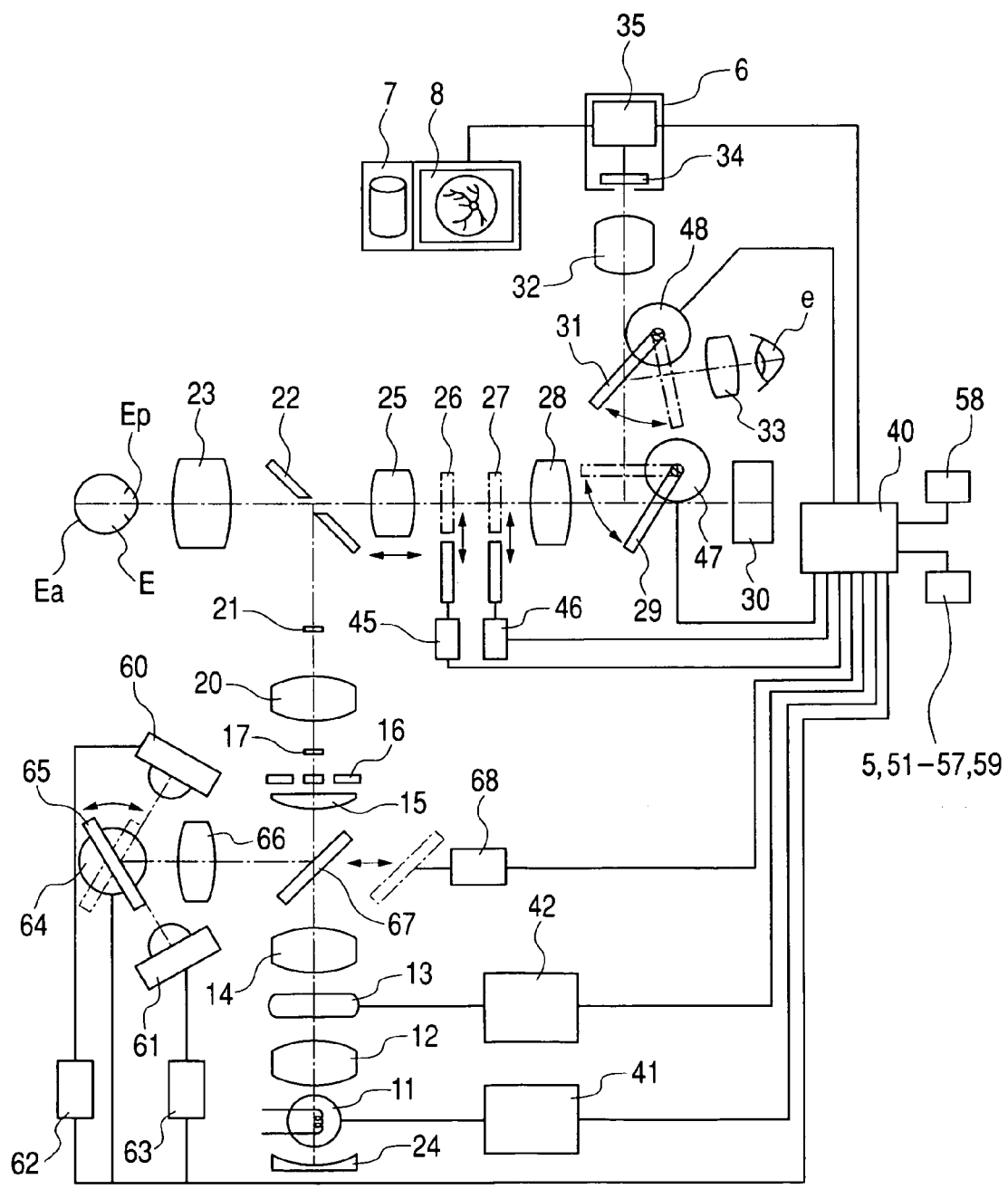
FIG. 16 shows the optical and electrical configuration of the device of another embodiment of the invention.

FIG. 16 shows a method using as light sources for fluorescence contrast illumination laser beam sources comprising an infrared laser beam generator 60 and a visible laser beam generator 61 instead of a combination of the watch light source 11 or the photographic light source 13 and the visible fluorescence exciter filter 18 or the infrared fluorescence exciter filter 19. The infrared laser beam generator 60 and the visible laser beam generator 61 are driven by infrared light emission control means 62 and visible light emission control means 63, respectively, and controlled by the control means 40.

In the emitting direction of the two laser beam generator 60 and 61, there is arranged a rotating mirror 65 which selectively reflects laser beams from these generators and driven by the drive means 64, and in the reflecting direction of the rotating mirror 65 are arrayed an expansion lens 66 and a mirror 67. The mirror 67 can be positioned on or off an illumination optical path between the condenser lens 12 and the field lens 15 by an actuator 68.

For instance in the infrared fluorescence contrast mode, the mirror 67 is positioned on the illumination optical path, the rotating mirror 65 installed to be rotatable by the drive means 64 is set at a prescribed angle, and the infrared laser beam generator 60 generating the light of the excitation wavelength for the infrared fluorescence contrast medium is caused to start emission by the infrared light emission control means 62. The infrared laser beam so generated is guided by the rotating mirror 65 to the expansion lens 66 and, with its beam diameter being varied to a prescribed size, guided by the mirror 67 to the field lens 15.

In the alignment mode, the infrared fluorescence barrier filter 27 is not positioned on the optical path, and the infrared light emission control means 62 keeps the emission intensity of the infrared laser beam extremely low. In the fluorescent moving image mode, the infrared fluorescence barrier filter 27 is positioned on the optical path, and the emission intensity of the infrared laser beam is increased by a prescribed quantity. In the fluorescent still image mode, if the emission intensity is so controlled as to momentarily increase the emission intensity of the infrared laser beam, the gain control of the electronic image pickup element 34 can be accomplished in the same way as described above.

To add, visible fluorescence contrast photography can be controlled in the same way as infrared fluorescence contrast photography by using the visible laser beam generator 61 generating the light of the excitation wavelength for the visible fluorescence contrast medium.

As hitherto described, the ophthalmologic photographic device according to the present invention makes it possible, in photography with a fixed gain and AGC switched between each other as appropriate, to achieve a proper gain promptly in switching from a fixed gain to AGC and thereby to obtain an appropriate image instantaneously.

Setting the same AGC gain used before a mode shift as the start gain for resumed AGC contributes to reducing the length of time taken for setting and accordingly to rapid stabilization of the gain.

Predictive setting of the AGC start gain by utilizing a plurality of AGC gains used before a mode shift is effective when the light intensity of the object of photography significantly varies, such as in a situation where a long time is taken to shift again to AGC.

Predictive setting of the AGC start gain from the gain and light intensity in still image taking is effective when the gain and light intensity have been varied, such as in consecutive taking of still images, and the use of exciter filters in the exciting light source together with a lamp and a strobe contributes to economy.

Where a laser beam is used as the exciting light, greater safety can be ensured because the step S/N is increased by reducing the gain and the light intensity is increased momentarily only when an image of high quality is desired.

What is claimed is:

1. An ophthalmologic photographic device comprising:
   (1) electronic image pickup means for photographing the eye to be examined;
   (2) amplifying means for amplifying signals from said image pickup means;
   (3) amplification rate varying means for varying the amplification rate of said amplifying means; and
   (4) amplification mode switching means for switching an amplifying mode of amplifying the signals in the amplifying means, between a fixed amplification mode wherein the signals are amplified using a fixed amplification rate and an automatic amplification mode wherein the signals are amplified using a varied amplification rate which is automatically varied by the amplification rate varying means, wherein:
   in a case that after the amplification mode switching means switches the amplifying mode from a firstly set automatic amplification mode to the fixed amplification mode, the amplifying mode is switched from the thus set fixed amplification mode to a secondly set automatic amplification mode, wherein the amplification rate varying means varies the amplification rate at the time of starting the secondly set automatic amplification mode on the basis of the amplification rate in the firstly set automatic amplification mode.

2. The ophthalmologic photographic device according to claim 1 further including:
   moving image mode/still image mode switching means for switching between a moving image mode and a still image mode, wherein:
   image picking-up is accomplished in said automatic amplification mode when in the moving image mode and in said fixed amplification mode when in the still image mode.

3. The ophthalmologic photographic device according to claim 2 wherein:
   amplification mode switching means further has an alignment mode, in which an image is taken in the fixed amplification mode.

4. The ophthalmologic photographic device according to claim 1 wherein:
   amplification mode switching means further has an alignment mode, in which an image is taken in the fixed amplification mode.

5. The ophthalmologic photographic device according to claim 1 wherein:
   an initial amplification rate at the time of switching from said fixed amplification mode to the automatic amplification mode again is determined from a plurality of amplification rates set within a prescribed period of time.

* * * * *